(12) United States Patent
Smithyman et al.

(10) Patent No.: US 9,107,418 B2
(45) Date of Patent: Aug. 18, 2015

(54) ANIMAL LESION TREATMENT AND PREVENTION FORMULATIONS AND METHODS

(71) Applicant: Zoetis LLC, Florham Park, NJ (US)

(72) Inventors: Dennis Smithyman, Shreveport, LA (US); Rosemary Smithyman, Shreveport, LA (US); Stephen P. Mixon, Sr., Fairhope, AL (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 13/899,994

(22) Filed: May 22, 2013

(65) Prior Publication Data

US 2013/0330420 A1     Dec. 12, 2013

Related U.S. Application Data

(63) Continuation of application No. 12/589,097, filed on Oct. 16, 2009, now abandoned.

(60) Provisional application No. 61/209,906, filed on Mar. 12, 2009.

(51) Int. Cl.
| | |
|---|---|
| *A01N 59/16* | (2006.01) |
| *A01L 15/00* | (2006.01) |
| *A01N 59/00* | (2006.01) |
| *A01N 59/02* | (2006.01) |
| *A61K 9/00* | (2006.01) |
| *A61K 33/06* | (2006.01) |
| *A61K 33/30* | (2006.01) |
| *A61K 33/34* | (2006.01) |
| *A61K 33/38* | (2006.01) |
| *A61K 45/06* | (2006.01) |
| *A61K 9/16* | (2006.01) |

(52) U.S. Cl.
CPC ............... *A01N 59/16* (2013.01); *A01L 15/00* (2013.01); *A01N 59/00* (2013.01); *A01N 59/02* (2013.01); *A61K 9/0014* (2013.01); *A61K 33/06* (2013.01); *A61K 33/30* (2013.01); *A61K 33/34* (2013.01); *A61K 33/38* (2013.01); *A61K 45/06* (2013.01); *A61K 9/1611* (2013.01)

(58) Field of Classification Search
CPC ....... A01N 59/02; A01N 59/00; A01N 59/16; A01N 59/20; A61K 33/30; A61K 33/06; A61K 33/34; A61K 9/0014; A61K 9/1611; A01L 15/00
See application file for complete search history.

(56) References Cited

U.S. PATENT DOCUMENTS

| | | | |
|---|---|---|---|
| 3,991,218 A | 11/1976 | Earle et al. | |
| 4,268,504 A | 5/1981 | Harrington et al. | |
| 4,822,595 A | 4/1989 | Corliss et al. | |
| 5,070,105 A | 12/1991 | Segall et al. | |
| 5,200,189 A | 4/1993 | Oakes et al. | |
| 5,658,467 A | 8/1997 | LaZonby et al. | |
| 5,683,724 A | 11/1997 | Hei et al. | |
| 5,772,985 A | 6/1998 | Kemp et al. | |
| 5,989,595 A | 11/1999 | Cummins | |
| 6,028,104 A | 2/2000 | Schmidt et al. | |
| 6,242,011 B1 | 6/2001 | Cummins | |
| 6,251,386 B1 | 6/2001 | Johansen | |
| 6,444,707 B1 | 9/2002 | Lampe et al. | |
| 6,514,556 B2 | 2/2003 | Hilgren et al. | |
| 6,534,075 B1 | 3/2003 | Hei et al. | |
| 6,994,890 B2 | 2/2006 | Ohlhausen et al. | |
| 7,026,308 B1 | 4/2006 | Gavin et al. | |
| 7,049,339 B2 | 5/2006 | Thomson | |
| 7,060,302 B1 | 6/2006 | Hickok | |
| 7,097,861 B1 | 8/2006 | O'Brien | |
| 7,163,709 B2 | 1/2007 | Cook et al. | |
| 7,192,618 B2 | 3/2007 | Cummins et al. | |
| 7,354,888 B2 | 4/2008 | Mosteller | |
| 7,510,721 B2 | 3/2009 | Roden et al. | |
| 7,927,510 B2 | 4/2011 | Mullins et al. | |
| 8,012,511 B1 | 9/2011 | Cummins et al. | |
| 2004/0175433 A1 | 9/2004 | Thomson | |
| 2006/0286229 A1 | 12/2006 | Koefod et al. | |
| 2007/0128295 A1 | 6/2007 | Kennedy | |
| 2007/0269563 A1 | 11/2007 | Mixon et al. | |
| 2008/0121189 A1 | 5/2008 | Greeson | |
| 2008/0166424 A1 | 7/2008 | Mixon et al. | |
| 2008/0213444 A1 | 9/2008 | Mixon et al. | |
| 2008/0292725 A1 | 11/2008 | Mixon, Sr. et al. | |
| 2009/0110751 A1 | 4/2009 | Kenneke | |
| 2009/0192231 A1 | 7/2009 | Lemons | |

OTHER PUBLICATIONS

Quilo et al., The impact of single antimicrobial intervention treatment with potassium lactate, sodium metasilicate, peroxyacetic acid, and acidified sodium chlorite on noninoculated ground beef lipid, instrumental color, and sensory characteristics, Meat Science, 2009, pp. 345-350, vol. 83.

Stivarius et al., Effects of hot water and lactic acid treatment of beef trimmings prior to grinding on microbial, instrumental color and sensory properties of ground beef during display, Meat Science, 2002, pp. 327-334, vol. 60.

Stivarius et al., The effects of acetic acid, gluconic acid and trisodium citrate treatment of beef trimmings on microbial, color and odor characteristics of ground beef through simulated retail display, Meat Science, 2002, pp. 245-252, vol. 60.

Stivarius et al., Microbial, instrumental color and sensory color and odor characteristics of ground beef produced from ground beef trimmings treated with ozone or chlorine dioxide, Meat Science, 2002, pp. 299-305, vol. 60.

Swarbrick et al., Drug permeation through human skin II: Permeability of ionizable compounds, Journal of Pharmaceutical Sciences, 1984, pp. 1352-1355, vol. 73, No. 10.

*Primary Examiner* — Abigail Fisher
*Assistant Examiner* — Daniel L Branson
(74) *Attorney, Agent, or Firm* — Vyacheslav V. Vasilyev

(57) ABSTRACT

An illustrative embodiment of an animal lesion treatment and prevention formulation includes a quantity of water, at least one acid provided in the quantity of water and magnesium sulfate as acid/base buffer mixed in the quantity of water with the at least one acid. In some embodiments, an antimicrobial agent comprising at least one antimicrobial metal salt may be provided in the quantity of water with the at least one acid and the magnesium sulfate.

10 Claims, 10 Drawing Sheets

Footbath Treatment

Topical Treatment

FIG. 3–Surface Treatment

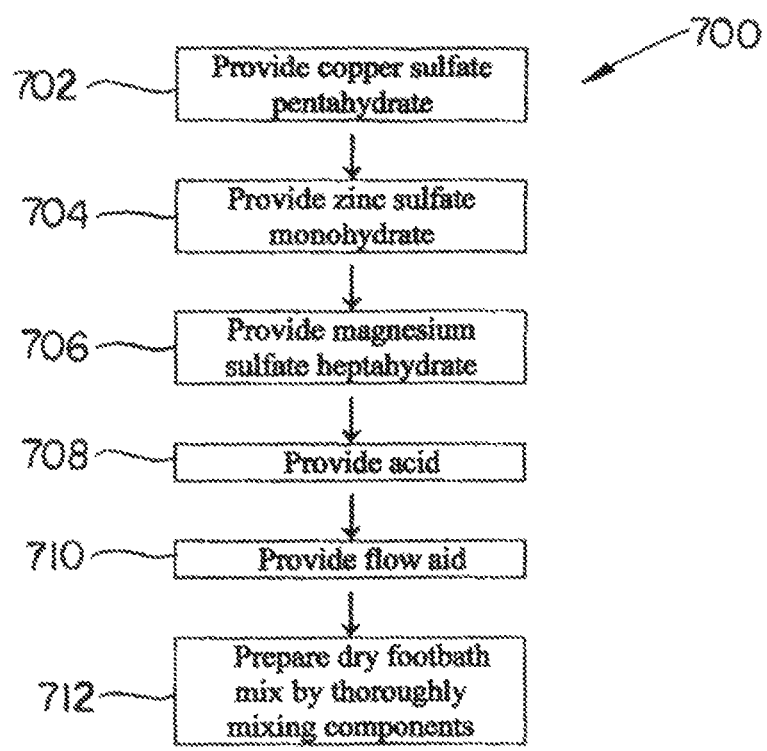
FIG. 7-Dry Footbath Mix Preparation

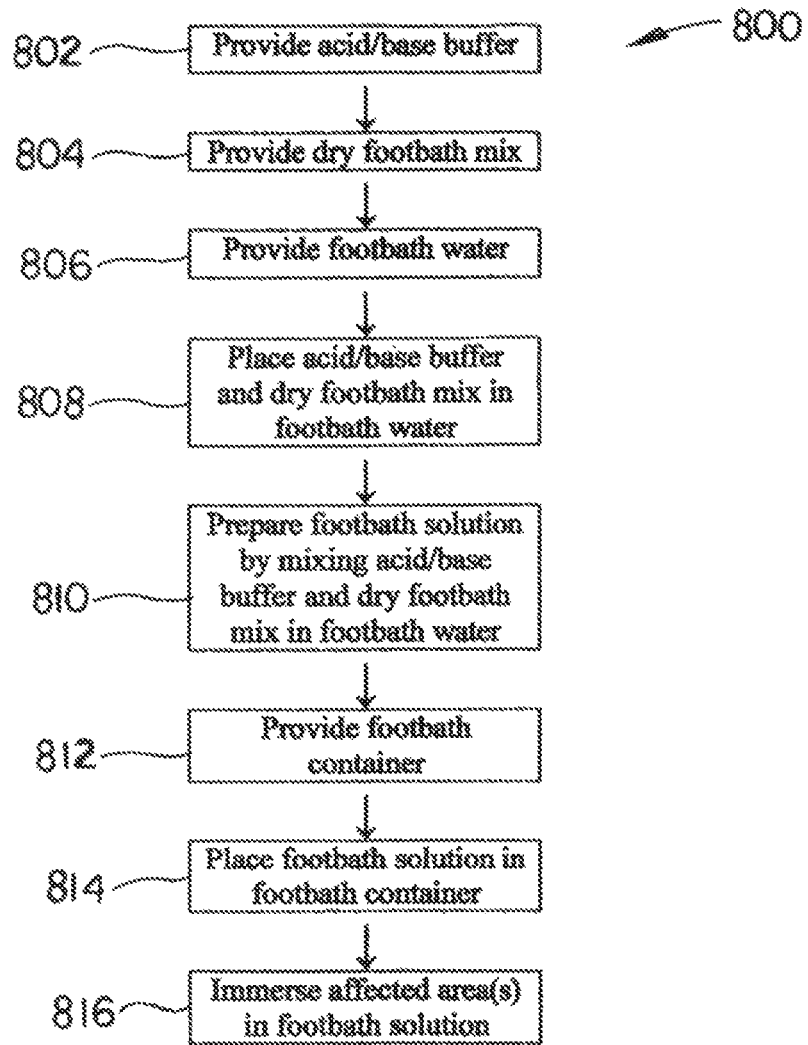
FIG. 8-Footbath Treatment
(Dry Footbath Mix)

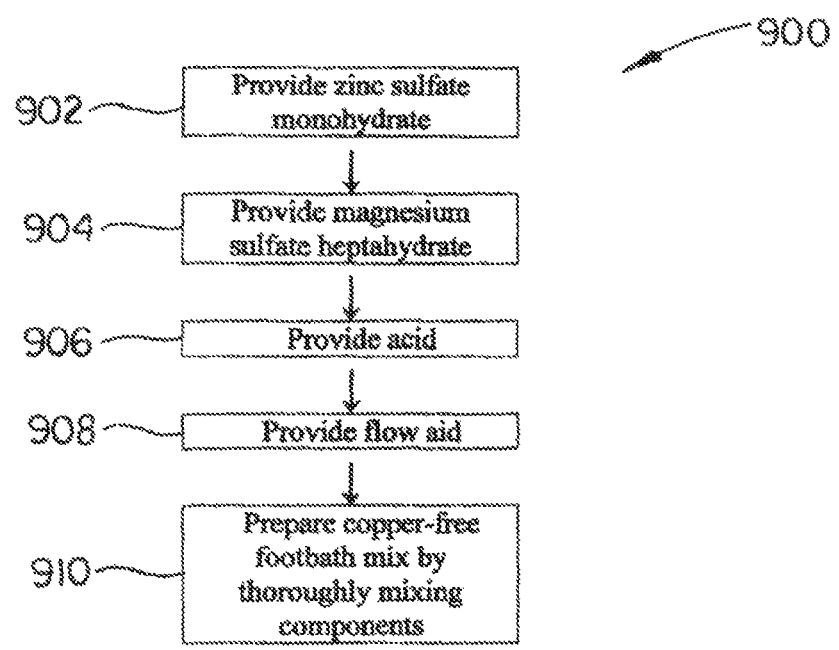
FIG. 9-Copper-Free Footbath Mix Preparation

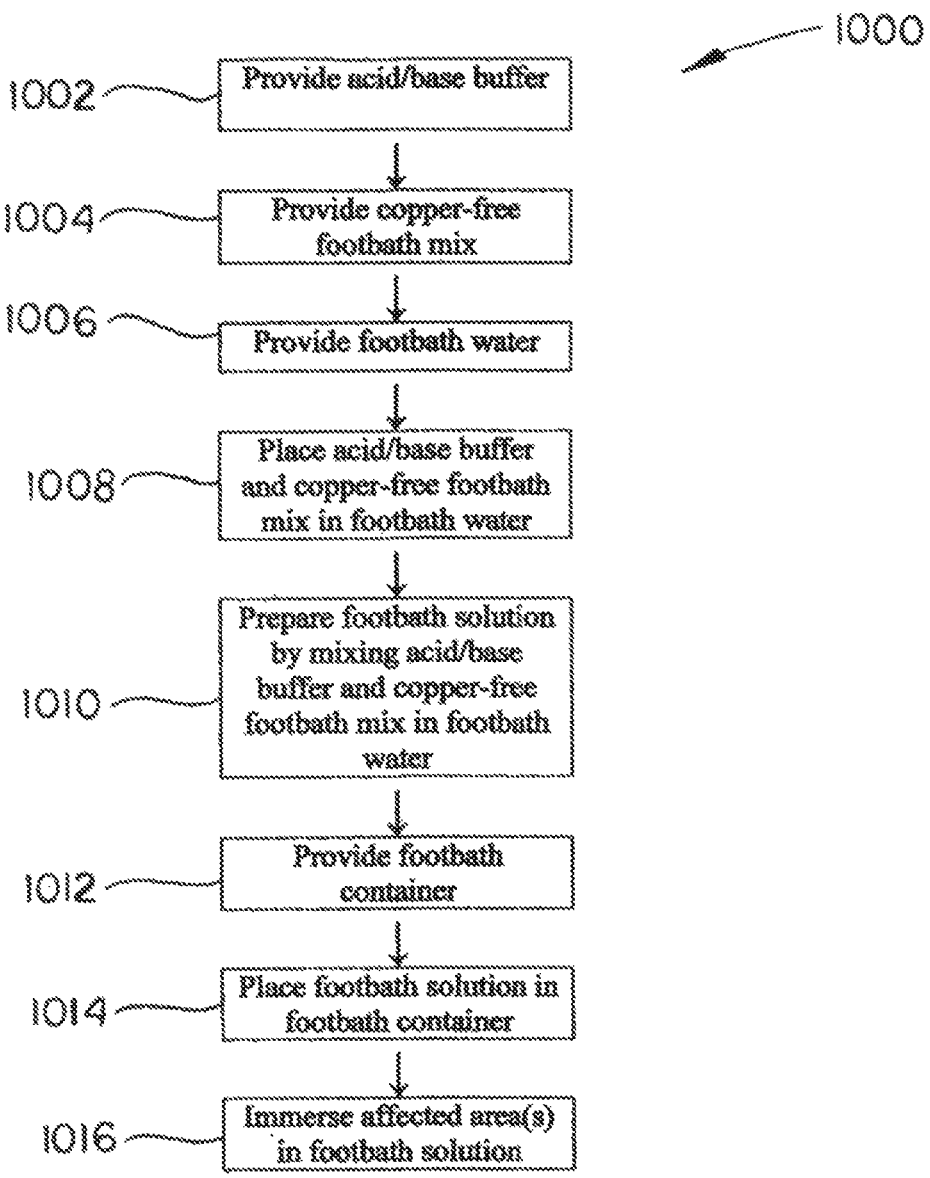
FIG. 10-Footbath Treatment
(Copper-Free Footbath Mix)

ANIMAL LESION TREATMENT AND PREVENTION FORMULATIONS AND METHODS

CROSS-REFERENCE TO RELATED APPLICATIONS

This application is a Continuation of U.S. Nonprovisional application Ser. No. 12/589,097 filed 16 Oct. 2009 which claims the benefit of and incorporates by reference in its entirety U.S. Provisional Application No. 61/209,906 filed 12 Mar. 2009.

TECHNICAL FIELD

The present disclosure generally relates to formulations and methods for treatment and prevention of infectious bacterial conditions and lesions on animals such as livestock. More particularly, the present disclosure relates to animal lesion treatment and prevention formulations and methods having enhanced acid/base buffering capability.

BACKGROUND

Conditions of the feet of animals, particularly ungulates, include such maladies as hairy heel warts, foot rot and foot scald and may present major health problems that can cause tremendous economic losses to producers of livestock. Lameness in cattle as a result of these conditions may result in loss of weight and body conditioning. In dairy cattle, milk production may be lowered because the animals may tend to go to feed less often. While conditions of the hoof are most prevalent in dairy cattle, beef cattle, goats and sheep, horses and other hoofed animals may be susceptible to the microbes which cause these conditions.

Papillomatous digital dermatitis (also known as Hairy Heel Warts), Footwarts and Strawberry Foot Diseases are inflammatory conditions which affect the skin around the hoof of an animal. These conditions commonly affect the back of the foot between the bulbs of the heels, but can spread around the foot and into the cleft between the claws. Digital dermatitis is a painful condition which may result in lameness, reduced food intake and fertility. Dairy cattle infected with the condition may also have reduced milk yields. Within a given herd, the proportion of animals affected by digital dermititis can remain at low levels of less than 10% while in others, over half of the animals of the herd can be affected. The severity of the condition may also vary according to location.

The precise cause of digital dermatitis is not known, but it is known that the condition is infectious in origin and that spiral bacteria are found in the lesions whereas they are not normally found in healthy skin. In fact, some strains of the condition are consistently found deep in damaged skin.

Foot rot, or infectious pododermatitis, is a hoof infection that is commonly found in cattle, sheep and goats. The condition rots away the foot of the animal, more specifically the area between the toes. Like digital dermatitis, foot rot is extremely painful and contagious.

In cattle, the cause of foot rot is thought to be one of two types of anaerobic bacteria, *Fusobacterium necrophorum* and *Bacteroides melaminogenicus*. Both types of bacteria are common in the environment in which cattle live. *Fusobacterium* is present in the rumen and fecal matter of cattle. Foot rot may also be caused by the microorganism *Diechelobacter nodosus*, which can be found in contaminated soil. Another cause of foot rot may include high temperatures or humidity, which may cause the skin between the hooves to crack and harbor infectious bacteria. Foot rot is prevalent in the southern region of the United States due to the wet and humid climate in that part of the country. If untreated, foot rot can spread to an adjacent joint, often resulting in the loss of the animal.

Foot scald, also known as benign foot rot or interdigital dermatitis, results in inflammation between the toes of an animal caused by the bacterium *F. necrophorum*. Persistent moisture on the skin between the toes can increase susceptibility to foot scald. which often precedes hoof rot. Like hoof rot, foot scald outbreaks occur most often during persistent rainy weather and high temperatures. If not treated, animals afflicted with foot scald may become permanently infected. As with other infectious conditions of the hoof, foot scald causes stress to the animals and can adversely affect weight gain, reproductive rates and production. Additionally, foot scald may incur additional costs to the livestock producer due to treatment and increased labor during an outbreak. Introducing an infected animal into an uninfected herd can create herd contamination and necessitate the treatment of all affected animals, including the previously-healthy ones, in the herd.

One method of treating foot, hoof, leg and other lesions in livestock and other animals includes preparation of an acidic antimicrobial footbath which may contain ions of an antimicrobial metal salt such as copper or zinc, for example, in an acidic solution such as aqueous sulfuric acid. The animals may be walked through the footbath at regular intervals such that the antimicrobial activity of the metal ions in the solution kills microbes which may otherwise cause or exacerbate the severity of lesions on the hoofs, feet and/or legs of the animals. The antimicrobial efficacy of the footbath solution requires complete or near complete dissolution of the metal ions in the solution. Dissolution of the metal ions to an extent which maintains their antimicrobial activity in the footbath solution requires that the solution be maintained at a pH of from about 1.0 to about 6.0 depending on the metal ion. Moreover, a pH increase above these levels causes the metal ions to precipitate out of solution and consequently, the antimicrobial properties of the footbath are reduced. In addition, the precipitated metal may accumulate in the soil to levels which are toxic to soil microbes and crops. Soil toxicity may slow decomposition of organic matter and nutrient cycling in soil and consequently, compromise soil production and fertility.

As the livestock or other animals are walked through the footbath as part of the treatment regimen, organic loads including feces from the livestock or animals often drop into the footbath, raising the pH of the footbath solution. Therefore, it may be necessary to provide an acid/base buffer in the bath solution to maintain the low pH of the solution and complete or near-complete dissolution of the metal ions in solution. Moreover, the presence of an acid/base buffer in the bath solution renders the solution compatible with human health and less irritating to skin and less corrosive to metals and concrete. In animals with healthy hooves, the formulation may help prevent digital dermatitis and interdigital phlegmon (foot rot) by maintaining healthy hoof conditions. The drying properties of the formulation may enhance hoof hardness and render soft tissue of hooves invulnerable to bacterial infection.

Accordingly, animal lesion treatment and prevention formulations and methods having enhanced acid/base buffering capability are needed.

SUMMARY

The present disclosure is generally directed to animal lesion treatment and prevention formulations having enhanced acid/base buffering capability. An illustrative embodiment of the formulation includes a quantity of water; at least one acid provided in the quantity of water; and magnesium sulfate as acid/base buffer mixed in the quantity of water with the at least one acid. In some embodiments, an antimicrobial agent comprising at least one antimicrobial metal salt may be provided in the water with the acid and the magnesium sulfate solution.

The present disclosure is further generally directed to animal lesion treatment and prevention methods which utilize animal lesion treatment and prevention formulations having enhanced acid/base buffering capability. An illustrative embodiment of the animal lesion treatment and prevention method includes providing an aqueous formulation solution comprising at least one acid and magnesium sulfate as an acid/base buffer; providing an animal having at least one lesion; and treating the at least one lesion or area on the animal which may be susceptible to lesions with the formulation solution. In some embodiments, an antimicrobial agent comprising at least one antimicrobial metal salt may be provided in the aqueous formulation solution. In some embodiments, the formulation may be used as a prophylactic to prevent infections on animals without lesions.

The present disclosure is further generally directed to surface sanitation treatment methods which utilize animal lesion treatment and prevention formulations having enhanced acid/base buffering capability. An illustrative embodiment of the surface sanitation treatment method includes providing an aqueous formulation solution comprising at least one acid and magnesium sulfate as an acid/base buffer; providing at least one surface; and applying the formulation solution to the at least one surface. The surface which is treated may be soft tissue or a hard surface, for example and without limitation. In some embodiments, an antimicrobial agent comprising at least one antimicrobial metal salt may be provided in the aqueous formulation solution.

The present disclosure is further generally directed to a dry formulation mix which may be added to an acid/base buffer and water to form a formulation solution. An illustrative embodiment of the dry formulation mix includes a selected quantity of zinc sulfate monohydrate and a selected quantity of magnesium sulfate heptahydrate mixed with the zinc sulfate monohydrate.

The present disclosure is further generally directed to an animal lesion treatment and prevention formulation. An illustrative embodiment of the formulation includes a formulation solution comprising a supply of water, an acid/base buffer provided in the supply of water and a formulation mix provided in the supply of water with the acid/base buffer and comprising a selected quantity of zinc sulfate monohydrate and a selected quantity of magnesium sulfate heptahydrate mixed with the zinc sulfate monohydrate.

The present disclosure is further generally directed to an animal lesion treatment and prevention method. An illustrative embodiment of the method includes providing an aqueous formulation solution comprising an acid/base buffer and a formulation mix comprising a selected quantity of zinc sulfate monohydrate and a selected quantity of magnesium sulfate heptahydrate mixed with the zinc sulfate monohydrate; providing an animal having at least one lesion; and treating the at least one lesion with the formulation solution.

BRIEF DESCRIPTION OF THE DRAWINGS

The disclosure will now be made, by way of example, with reference to the accompanying drawings, in which:

FIG. 7 is a flow diagram which illustrates preparation of an illustrative embodiment of a dry footbath mix;

FIG. 8 is a flow diagram of an illustrative embodiment of the animal lesion treatment and prevention methods in which an illustrative footbath embodiment of the animal lesion treatment and prevention formulation is prepared using a dry footbath mix and a lesion-afflicted area or areas on an animal is/are treated with the formulation by immersing the affected area or areas in the footbath;

FIG. 9 is a flow diagram which illustrates preparation of an illustrative embodiment of a copper-free footbath mix; and FIG. 10 is a flow diagram of an illustrative embodiment of the animal lesion treatment and prevention methods in which an illustrative footbath embodiment of the animal lesion treatment and prevention formulation is prepared using a copper-free footbath mix and a lesion-afflicted area or areas on an animal is/are treated with the formulation by immersing the affected area or areas in the footbath.

DETAILED DESCRIPTION

Figure 1:
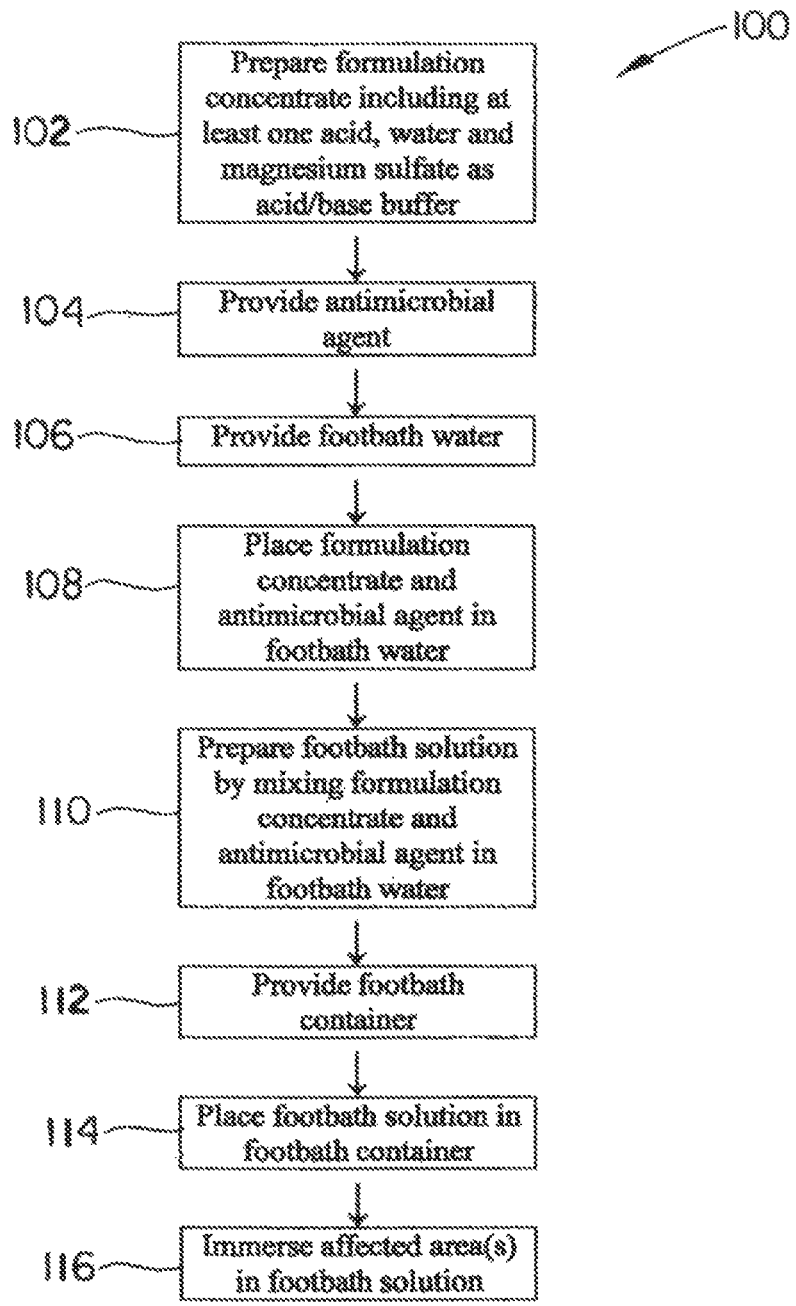
FIG. 1 is a flow diagram of an illustrative embodiment of the animal lesion treatment and prevention methods in which an illustrative footbath embodiment of the animal lesion treatment and prevention formulation is prepared and a lesion-afflicted area or areas on an animal is/are treated with the formulation by immersing the affected area or areas in the footbath.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to implement the disclosure and are not intended to limit the scope of the claims. Furthermore, there is no intention to be bound by any expressed or implied theory presented in the preceding technical field, background, brief summary or the following detailed description.

The present disclosure is generally directed to animal lesion treatment and prevention formulations having enhanced acid/base buffering capability. In some embodiments, the animal lesion treatment and prevention formulation may include an aqueous formulation solution having at least one acid such as sulfuric acid, a sulfuric acid derivative such as sulfamic acid and/or sodium bisulfate, for example and without limitation; magnesium sulfate as an acid/base buffer; and an antimicrobial agent including at least one antimicrobial metal salt. The magnesium sulfate acts as a buffer to maintain the pH of the formulation solution within a sufficiently low range to facilitate and maintain complete or almost complete dissolution of the antimicrobial metal salt ions in the formulation solution and therefore, sustain the antimicrobial properties of the antimicrobial metal salt and prevent or minimize precipitation of the antimicrobial metal salt out of solution. The magnesium sulfate may maintain the pH of the formulation solution within the desired pH range and act as a potent buffer against rising pH upon introduction of basic materials such as organic loads into the solution. The magnesium sulfate buffering of acid may also reduce skin irritation, promote drying of lesions and reduce corrosive effects of the solution on concrete and metal.

When applied to soft tissue foot lesions of bovines as part of a treatment regimen, the animal lesion treatment and prevention formulations do not tend to irritate the lesions, even when the pH of the formulations drop below 1.0 and may have a soothing effect. The formulations may promote healing of skin lesions by rapid drying of the lesions (progressing from open, moist and easily bleeding to closed, dark, dry and non-bleeding), rapid reduction in pain scores (resulting in improved animal mobility and consequent increase in feed/water intake and increased milk production) and shrinking of lesion margins (which may initially decrease in size and eventually disappear). In some embodiments, a formulation described herein has a pH less than 1.0.

In some embodiments, the antimicrobial metal salt or metals of the antimicrobial agent in the formulation solution may include copper, zinc, silver or any combination of those metals. In some embodiments, the antimicrobial agent may further include antimicrobial salts such as potassium chloride and/or sodium chloride, for example and without limitation.

In some embodiments, the magnesium sulfate may be provided in the form of magnesium sulfate heptahydrate ($MgSO_4 7H_2O$) as epsom salts.

In some embodiments, the animal lesion treatment and prevention formulation may be prepared and used as a formulation footbath solution in which one or more lesion-affected areas on an animal may be immersed as part of a treatment regimen. A formulation concentrate which includes at least one acid such as sulfuric acid, a sulfuric acid derivative such as sulfamic acid and/or sodium bisulfate, for example and without limitation, in addition to water and magnesium sulfate as an acid/base buffer, may initially be prepared. The formulation concentrate may be added, along with the antimicrobial agent, to a selected volume of footbath water. The formulation concentrate and the antimicrobial agent may be thoroughly mixed in the footbath water to obtain a substantially homogenous formulation footbath solution.

In some embodiments, the formulation concentrate of the formulation footbath solution may be prepared with such a concentration as to attain a starting pH in a range of from about 1.3 to about 2.5 when mixed with the footbath water to form the formulation footbath solution. The formulation concentrate may include sulfuric acid, a sulfuric acid derivative such as sulfamic acid and/or sodium bisulfate, for example and without limitation, in a concentration of up to about 52% by weight; magnesium sulfate in a concentration of from about 9% to about 11% by weight; and water in a concentration of from about 37% to about 41% by weight.

In some embodiments, the formulation concentrate of the formulation footbath solution may be prepared using sulfuric acid, a sulfuric acid derivative such as sulfamic acid and/or sodium bisulfate, for example and without limitation, in a concentration of about 51% by weight; magnesium sulfate in a concentration of about 10% by weight; and water in a concentration of about 39% by weight.

In some embodiments, the formulation footbath solution may be prepared by adding the formulation concentrate to the footbath water in a quantity of from about 0.25 oz to about 0.75 oz formulation concentrate per gallon of footbath water. The antimicrobial metal salt(s) may be added to the footbath water in a concentration which is sufficient to impart antimicrobial properties to the formulation footbath solution. In some embodiments, the antimicrobial metal salt(s) may be present in the formulation footbath solution in a concentration of from about 0.1 lbs. per gallon to about 0.6 lbs. per gallon of footbath water.

In some embodiments, the animal lesion treatment and prevention formulation may be prepared and used as a topical spray, gel, cream, foam, lotion, powder, hide wash, shampoo or other topical formulation which may be topically applied to one or more lesion-affected areas on an animal as part of a treatment regimen for wounds, rain rot (rain scald and related conditions), thrush, white line disease and related conditions, for example and without limitation. A formulation concentrate which includes at least one acid such as sulfuric acid, a sulfuric acid derivative such as sulfamic acid and/or sodium bisulfate, for example and without limitation, in addition to water and magnesium sulfate as an acid/base buffer, may initially be prepared. The formulation concentrate, along with the antimicrobial agent, may be added to a selected volume of water. The formulation concentrate and the antimicrobial agent may be thoroughly mixed in the water to obtain a substantially homogenous topical formulation solution. The topical formulation solution may subsequently be subjected to additional processing steps to form a topical formulation which may be in a spray, gel, cream, foam, lotion, powder, hide wash, shampoo or other topical formulation form according to the knowledge of those skilled in the art. The final topical formulation may be applied to one or more lesion-affected areas on an animal as part of the treatment regimen.

In some embodiments, the formulation concentrate of the topical formulation may be prepared with a sufficient concentration to attain a starting pH of from about 1.0 to about 6.0 when mixed with water to form the topical formulation solution. The formulation concentrate may include sulfuric acid, a sulfuric acid derivative such as sulfamic acid and/or sodium bisulfate, for example and without limitation, in a concentration of from about 1% to about 55% by weight and magnesium sulfate in a concentration of from about 1% to about 25% by weight, with water being the balance of the formulation concentrate (from about 20% to about 94% by weight).

In some embodiments, the topical formulation solution may be prepared by adding the formulation concentrate to water. The antimicrobial metal salt(s) may be added to the water in a concentration which is sufficient to impart antimicrobial properties to the topical formulation solution. In some embodiments, the antimicrobial metal salt(s) may be present in the topical formulation solution in a concentration of from about 0.1 lbs. per gallon to about 0.6 lbs. per gallon of water.

In some embodiments, the animal lesion treatment and prevention formulations may be prepared and used as a surface sanitation formulation which may be applied to a material, item or surface which may be susceptible to microbial contamination and/or for ammonia reduction (such as meat, produce or poultry litter, for example and without limitation) as part of surface sanitation treatment, ammonia and/or other odor reduction and/or microbial contamination preventative measures. The formulation may be amenable to both dry and liquid applications. A formulation concentrate which includes at least one acid such as sulfuric acid, a sulfuric acid derivative such as sulfamic acid and/or sodium bisulfate, for example and without limitation, in addition to water and magnesium sulfate as an acid/base buffer, may initially be prepared. The formulation concentrate, along with the antimicrobial agent, may be added to a selected volume of water. The formulation concentrate and the antimicrobial agent may be thoroughly mixed in the water to obtain a substantially homogenous surface sanitation formulation solution. The surface sanitation formulation solution may subsequently be subjected to additional processing steps to form a surface sanitation formulation spray or other liquid surface sanitation formulation, according to the knowledge of those skilled in the art. The final surface sanitation formulation may be applied to a material, item or surface which may be susceptible to microbial contamination to kill microbes, prevent microbial contamination and/or facilitate odor reduction in or on the material, item or surface.

In some embodiments, the formulation concentrate of the surface sanitation formulation may be prepared with a sufficient concentration to attain a starting pH of from about 1.0 to about 6.0 when mixed with water to form the surface sanitation formulation solution. The formulation concentrate may include sulfuric acid, a sulfuric acid derivative such as sulfamic acid and/or sodium bisulfate, for example and without limitation, in a concentration of from about 1% to about 55% by weight and magnesium sulfate in a concentration of from about 1% to about 25% by weight, with water being the balance of the formulation concentrate (from about 20% to about 94% by weight).

The present disclosure is further generally directed to animal lesion treatment and prevention methods using animal lesion treatment and prevention formulations having enhanced acid/base buffering capability. In some embodiments, the animal lesion treatment and prevention method includes providing the animal lesion treatment and prevention formulation as an aqueous solution having at least one acid such as sulfuric acid, a sulfuric acid derivative such as sulfamic acid and/or sodium bisulfate, for example and without limitation; magnesium sulfate as an acid/base buffer; and an antimicrobial agent including at least one antimicrobial metal salt; and treating one or more lesion-affected areas on an animal with the animal lesion treatment and prevention formulation.

In some embodiments, the animal lesion treatment and prevention method may include preparing the animal lesion treatment and prevention formulation as an aqueous footbath solution and immersing one or more of the lesion-affected areas on the animal in the footbath solution.

In some embodiments, the footbath solution may be prepared by preparing a formulation concentrate including at least one acid, water and magnesium sulfate as an acid/base buffer; adding the formulation concentrate and an antimicrobial agent including at least one antimicrobial metal salt to footbath water; and mixing the formulation concentrate and the antimicrobial agent in the footbath water.

In some embodiments, the animal lesion treatment and prevention method may include preparing an animal lesion treatment and prevention formulation as a topical formulation in the form of a topical spray, gel, cream, foam, lotion, powder, hide wash, shampoo or other topical formulation or other form and applying the topical formulation to one or more lesion-affected areas on an animal.

In some embodiments, the topical formulation may be prepared by preparing a formulation concentrate including at least one acid, water and magnesium sulfate as an acid/base buffer; adding the formulation concentrate and an antimicrobial agent including at least one antimicrobial metal salt to footbath water; forming a topical formulation solution by mixing the formulation concentrate and the antimicrobial agent in the footbath water; and subjecting the topical formulation solution to additional processing step(s) to obtain the final topical formulation.

In some embodiments, the animal lesion treatment and prevention method may include preparing an animal lesion treatment and prevention formulation as a surface sanitation formulation and/or ammonia reduction agent in the form of a topical spray or other form and applying the surface sanitation formulation to a material, item or surface which may be susceptible to microbial contamination (such as meat, produce or poultry litter, for example and without limitation).

In some embodiments, the surface sanitation formulation may be prepared by preparing a formulation concentrate including at least one acid, water and magnesium sulfate as an acid/base buffer; adding the formulation concentrate and an antimicrobial agent including at least one antimicrobial metal salt to footbath water; forming a surface sanitation formulation solution by mixing the formulation concentrate and the antimicrobial agent in the footbath water; and subjecting the surface sanitation formulation solution to additional processing step(s) to obtain the final topical formulation.

Referring initially to FIG. 1 of the drawings, a flow diagram 100 illustrates an exemplary embodiment of the animal lesion treatment and prevention method. According to the animal lesion treatment and prevention method 100, the animal lesion treatment and prevention formulation is prepared as a footbath solution and a lesion-afflicted area or areas, or an area or areas which may be vulnerable to the development of lesions, on an animal is/are treated with the formulation by immersing the affected area or areas on the animal in the footbath solution. In block 102, a formulation concentrate which includes at least one acid, water and magnesium sulfate as an acid/base buffer is prepared. In block 104, an antimicrobial agent having at least one antimicrobial metal salt is provided. In block 106, footbath water is provided. In block 108, the formulation concentrate which was prepared in block 102 and the antimicrobial agent provided in block 104 are placed in the footbath water. In block 110, a footbath solution is prepared by mixing the formulation concentrate and the antimicrobial agent in the footbath water. In block 112, a footbath container is provided. In block 114, the footbath solution is placed in the footbath container. In some applications, the footbath solution may be prepared in the footbath container rather than being prepared outside the footbath container and then placed therein. In block 116, one or more lesion-affected areas on an animal is/are immersed in the footbath solution.

In some embodiments, the antimicrobial metal salt or metals of the antimicrobial agent provided in block 104 may include copper, zinc, silver or any combination of those metals. In some embodiments, the antimicrobial agent provided in block 104 may further include antimicrobial salts such as potassium chloride and/or sodium chloride, for example and without limitation.

In some embodiments, the formulation concentrate which is prepared in block 102 may impart a starting pH of about 1.5 to the footbath solution when mixed with the footbath water in block 110. The formulation concentrate may include sulfuric acid, a sulfuric acid derivative such as sulfamic acid and/or sodium bisulfate, for example and without limitation, in a concentration of up to about 52% and preferably, about 51% by weight; magnesium sulfate in a concentration of from about 9% to about 11% and preferably, about 10% by weight; and water in a concentration of from about 37% to about 41% and preferably, about 39% by weight. In some embodiments, preparation of the footbath solution in block 110 may include placing the formulation concentrate in the footbath water in a quantity of about 0.5 oz formulation concentrate per gallon of footbath water in block 108. In some embodiments, a 0.5 oz sample of the formulation concentrate prepared in block 102 may include from about 0.25 oz to about 0.26 oz and preferably, about 0.255 oz sulfuric acid, a sulfuric acid derivative such as sulfamic acid and/or sodium bisulfate, for example and without limitation; from about 0.045 oz to about 0.055 oz and preferably, about 0.05 oz magnesium sulfate; and from about 0.185 oz to about 0.205 oz and preferably, about 0.195 oz water.

In block 108, the antimicrobial metal salt(s) of the antimicrobial agent may be placed in the footbath water in a concentration which is sufficient to impart antimicrobial properties to the formulation footbath solution. In some embodiments, the antimicrobial metal salt(s) may be present in the formulation footbath solution in a concentration of from about 0.3 lbs. per gallon to about 0.5 lbs. per gallon of footbath water. In some embodiments, antimicrobial salts may be present in the footbath solution in a concentration of from about 0.6 lbs. to about 1.0 lbs. per gallon of footbath water.

In some embodiments, placing the footbath solution which was prepared in block 110 in the footbath container 112, as indicated in block 114, may include placing about 40~70 gallons of the footbath solution into the footbath container.

In block 116, the lesion-afflicted area(s) or vulnerable area(s) on the animal may be immersed in the footbath solution as often as is necessary to prevent the development of lesions or promote healing of the lesions. In some embodiments, the animal may be walked through the footbath solution in the footbath container or the affected area or areas may be otherwise immersed in the footbath solution as often as needed for prevention or healing of the lesions.

Figure 2:
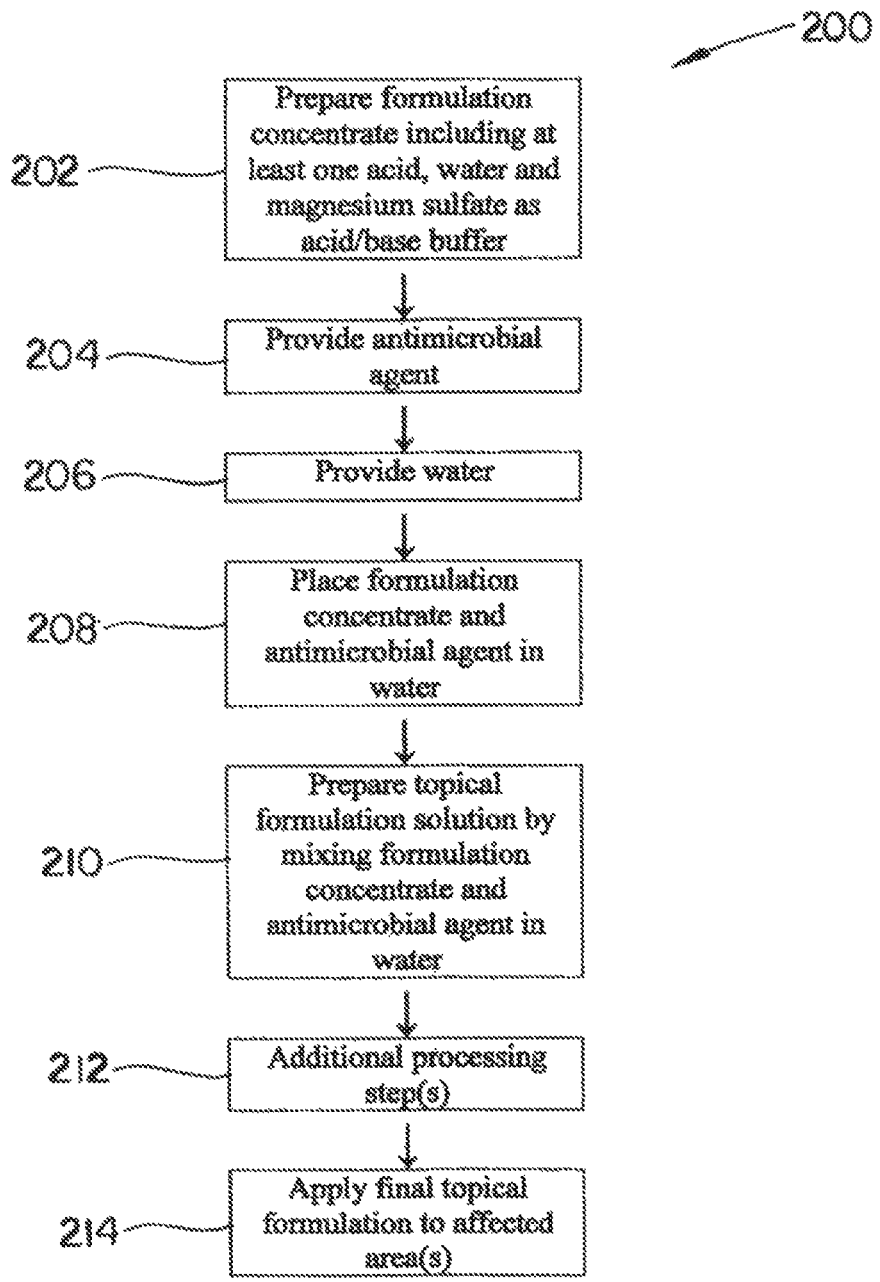
FIG. 2 is a flow diagram of an illustrative embodiment of the animal lesion treatment and prevention methods in which an illustrative topical formulation embodiment of the animal lesion treatment and prevention formulation is prepared and a lesion-afflicted area or areas on an animal is treated with the formulation by applying the topical formulation to the affected area or areas.

Referring next to FIG. 2 of the drawings, a flow diagram 200 illustrates another exemplary embodiment of the animal lesion treatment and prevention method. According to the animal lesion treatment and prevention method 200, the animal lesion treatment and prevention formulation is prepared as a topical formulation and a lesion-afflicted area or areas or vulnerable area(s) on an animal is/are treated with the topical formulation by topical application of the affected area or areas on the animal with the topical formulation. In block 202, a formulation concentrate which includes at least one acid, water and magnesium sulfate as an acid/base buffer is prepared. In block 204, an antimicrobial agent having at least one antimicrobial metal salt may be provided in some applications. In block 206, water is provided. In block 208, the formulation concentrate which was prepared in block 202 and the antimicrobial agent provided in block 204 are placed in the water. In block 210, a topical formulation solution is prepared by mixing the formulation concentrate and the antimicrobial agent in the water. In block 212, the topical formulation solution may be subjected to additional processing step(s) to transform the topical formulation solution into a topical spray, gel, cream, foam, lotion, powder, hide wash, shampoo or other topical formulation, according to the knowledge of those skilled in the art. In block 214, the final topical formulation is applied to one or more lesion-affected areas or one or more vulnerable area(s) on an animal as often as necessary to prevent the development of or promote healing of the lesions.

In some embodiments, the antimicrobial metal salt or metals of the antimicrobial agent provided in block 204 may include copper, zinc, silver or any combination of those metals. In some embodiments, the antimicrobial agent provided in block 204 may further include antimicrobial salts such as potassium chloride and/or sodium chloride, for example and without limitation.

In some embodiments, the formulation concentrate which is prepared in block 202 may impart a starting pH of from about 1.0 to about 6.0 to the topical formulation solution when mixed with the water in block 210. The formulation concentrate may include sulfuric acid, a sulfuric acid derivative such as sulfamic acid and/or sodium bisulfate, for example and without limitation, in a concentration of from about 1% to about 55% by weight and magnesium sulfate in a concentration of from about 1% to about 25% by weight, with the balance being water (which may be in a concentration of from about 20% to about 94% by weight). In some embodiments, preparation of the topical formulation solution in block 210 may include placing the formulation concentrate in the water in a quantity of about 0.5 oz formulation concentrate per gallon of water in block 208. In some embodiments, a 0.5 oz sample of the formulation concentrate prepared in block 202 may include from about 0.025 oz to about 0.275 oz sulfuric acid, a sulfuric acid derivative such as sulfamic acid and/or sodium bisulfate, for example and without limitation; from about 0.005 oz to about 0.125 oz magnesium sulfate; and from about 0.1 oz to about 0.47 oz water.

In block 208, the antimicrobial metal salt(s) of the antimicrobial agent may be placed in the water in a concentration which is sufficient to impart antimicrobial properties to the topical formulation solution. In some embodiments, the antimicrobial metal salt(s) may be present in the topical formulation solution in a concentration of from about 0.1 lbs. per gallon to about 0.6 lbs. per gallon of water. In some embodiments, antimicrobial salts may be present in the topical formulation solution in a concentration of from about 0.6 lbs. to about 1.0 lbs. per gallon of water.

Figure 3:
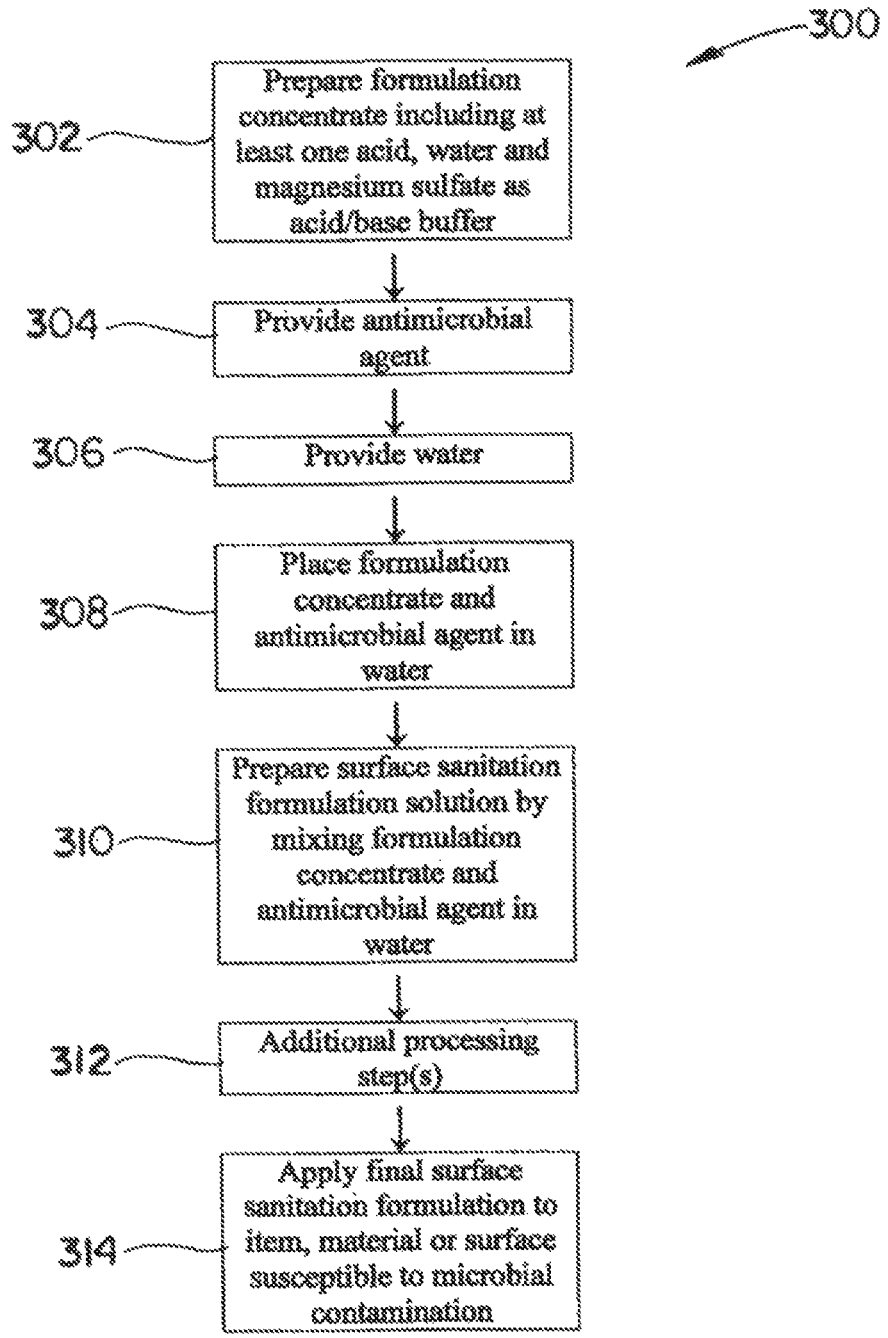
FIG. 3 is a flow diagram of an illustrative embodiment of the animal lesion treatment and prevention methods in which an illustrative surface sanitation formulation embodiment of the animal lesion treatment and prevention formulation is prepared and a material, item or surface which is susceptible to microbial contamination is treated with the surface sanitation formulation by applying the formulation to the material, item or surface.

Referring next to FIG. 3 of the drawings, a flow diagram 300 illustrates another exemplary embodiment of the animal lesion treatment and prevention method. According to the animal lesion treatment and prevention method 300, the animal lesion treatment and prevention formulation is prepared as a surface sanitation formulation. An item, material or surface which may be susceptible to microbial contamination, or a material requiring ammonia reduction, is treated with the surface sanitation formulation by topical application of the surface sanitation formulation to the item, material or surface. In block 302, a formulation concentrate which includes at least one acid, water and magnesium sulfate as an acid/base buffer is prepared. In block 304, an antimicrobial agent having at least one antimicrobial metal salt may be provided in some applications. In block 306, water is provided. In block 308, the formulation concentrate which was prepared in block 302 and the antimicrobial agent provided in block 304 are placed in the water. In block 310, a surface sanitation formulation solution is prepared by mixing the formulation concentrate and the antimicrobial agent in the water. In block 312, the surface sanitation formulation solution may be subjected to additional processing step(s) to transform the surface sanitation formulation solution into a topical spray other topical formulation which is suitable for application to the item, material or surface to be treated, according to the knowledge of those skilled in the art. In block 314, the final surface sanitation formulation is applied to an item, material or surface which may be susceptible to microbial contamination as often as necessary to prevent microbial contamination and/or for ammonia reduction purposes. The surface may be soft tissue of an animal or may be a hard surface.

In some embodiments, the antimicrobial metal salt or metals of the antimicrobial agent provided in block 304 may include copper, zinc, silver or any combination of those metals. In some embodiments, the antimicrobial agent provided in block 304 may further include antimicrobial salts such as potassium chloride and/or sodium chloride, for example and without limitation.

In some embodiments, the formulation concentrate which is prepared in block 302 may impart a starting pH of from about 1.0 to about 6.0 to the surface sanitation formulation solution when mixed with the water in block 310. The formulation concentrate may include sulfuric acid, a sulfuric acid derivative such as sulfamic acid and/or sodium bisulfate, for example and without limitation, in a concentration of from about 1% to about 55% by weight and magnesium sulfate in a concentration of from about 1% to about 25% by weight, with the balance being water (which may be in a concentration of from about 20% to about 94% by weight). In some embodiments, preparation of the surface sanitation formulation solution in block 310 may include placing the formulation concentrate in the water in a quantity of about 0.5 oz formulation concentrate per gallon of water in block 308. In some embodiments, a 0.5 oz sample of the formulation concentrate prepared in block 302 may include from about 0.025 oz to about 0.275 oz sulfuric acid, a sulfuric acid derivative such as sulfamic acid and/or sodium bisulfate, for example and without limitation; from about 0.005 oz to about 0.125 oz magnesium sulfate; and from about 0.1 oz to about 0.47 oz water.

In block 308, the antimicrobial metal salt(s) of the antimicrobial agent may be placed in the water in a concentration which is sufficient to impart antimicrobial properties to the surface sanitation formulation solution. In some embodiments, the antimicrobial metal salt(s) may be present in the surface sanitation formulation solution in a concentration of from about 0.1 lbs. per gallon to about 0.6 lbs. per gallon of water. In some embodiments, antimicrobial salts may be present in the surface sanitation formulation solution in a concentration of from about 0.6 lbs. to about 1.0 lbs. per gallon of water.

The animal lesion treatment and prevention formulations and methods will be better understood by consideration of the following examples, which are provided to illustrate and not limit the scope of the disclosure.

Example 1

Formulation Concentrate Preparation

A 32-ounce quantity of formulation concentrate was prepared by combining and thoroughly mixing 16.32 oz sulfuric acid and 3.20 oz magnesium sulfate in 12.48 oz water. The formulation concentrate was stored in a suitable container.

Example 2

On-Farm Trial Footbath Preparation

A 70-gallon volume of footbath solution was prepared as follows. A 32-ounce quantity (or quantity sufficient to achieve a target pH) of formulation concentrate which was prepared according to EXAMPLE 1 above was combined, along with 35 lbs. copper sulfate, to 70 gallons of footbath water. The formulation concentrate and the copper sulfate were thoroughly mixed in the footbath water to form a substantially homogenous footbath solution having a pH of 1.5.

Example 3

On-Farm Trial Procedure

The footbath solution which was prepared according to EXAMPLE 1 above was used to treat active foot warts (*Papillomatous digital dermatitis*) on a herd of Holstein dairy cattle. Prior to treatment, the warts on the cattle were examined. Initial assessment of the cattle included assessment of the rear heels of the cattle by recording ear tag numbers for all cattle (269 cows); spraying of the rear heels with water from a hose and recording of pain score on a scale of 0-3; visual inspection of rear heels using a flash light and recording of presence or absence, size, stage/severity, activity level and additional information including appearance. Seventy gallons of the footbath solution was placed in a footbath container. The cattle in the herd which were afflicted with foot warts were walked through the footbath solution once daily over a treatment period of two weeks. After each treatment, used footbath solution was discarded and fresh footbath solution was placed in the footbath container. After completion of the two-week treatment period, the cattle were again examined to determine the presence or absence of active warts on the cattle and the percentage of cattle in the herd afflicted with active foot warts, as well as the average pain score of the cattle after treatment.

Figure 4:
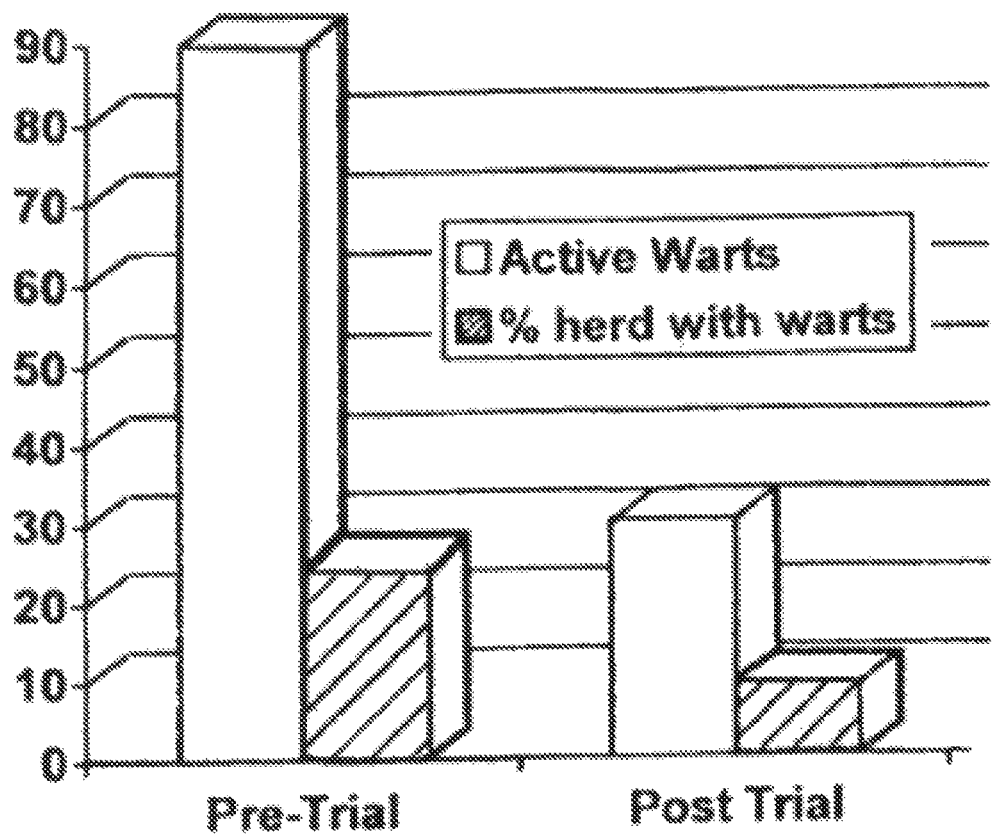
FIG. 4 is a bar graph which illustrates a comparison of the number of active foot warts and percentage of herd with active foot warts on dairy cattle in a herd before and after treatment with an illustrative embodiment of the animal lesion treatment and prevention formulation and method.

Comparisons of the number of active foot warts on the cattle and the percentage of the herd with active warts before and after treatment described in EXAMPLE 2 above are presented graphically in FIG. 4. Accordingly, treatment of the afflicted cattle resulted in a 67% reduction in the number of active warts on the cattle in the herd as well as a substantial reduction in the percentage of the herd which was afflicted with active foot warts.

Figure 5:
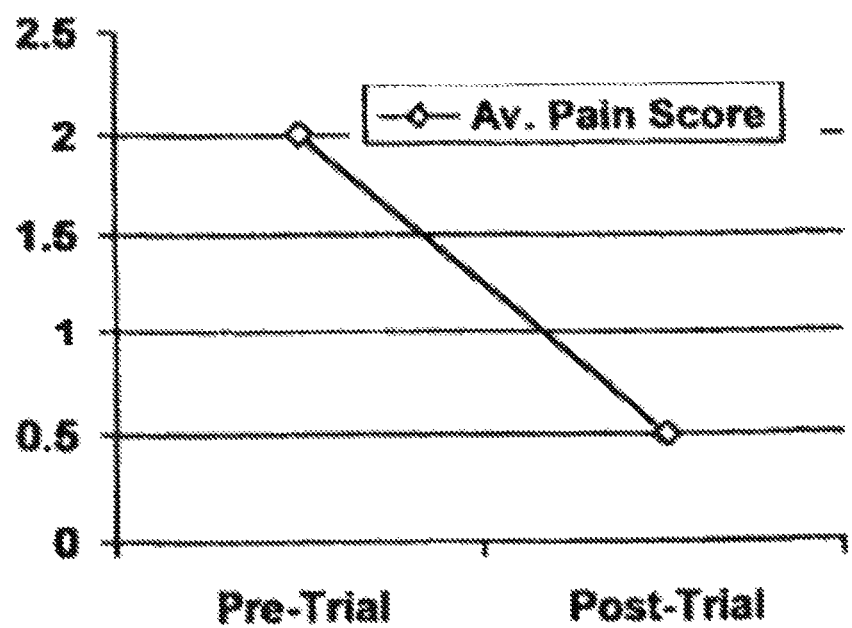
FIG. 5 is a line graph which illustrates a comparison of pain caused by active foot warts in dairy cattle before and after treatment with an illustrative embodiment of the animal lesion treatment and prevention formulation and method.

FIG. 5 is a line graph which illustrates a comparison of lesion pain in animals before and after the treatment described in EXAMPLE 2 above. There was a significant reduction in the level of pain (as determined by average pain score and visual inspection of hooves) caused by the foot warts in the afflicted cattle after treatment relative to the level of pain caused by the foot warts prior to treatment.

Example 4

Trial Surface Sanitation Formulation Preparation

Four test solutions of the surface sanitation formulation were prepared by adding a sufficient quantity of deionized water to the formulation concentrate which was prepared according to the method of EXAMPLE 1 above to obtain a first test solution having a pH of 4.0, a second test solution having a pH of 3.0, a third test solution having a pH of 2.0 and a fourth test solution having a pH of 1.0. A DI water control having a pH of 5.0 was also prepared. A fresh chicken carcass was obtained and exposed to ambient temperature overnight to allow microbial growth on the carcass. The carcass was then placed in a bird bag and washed using 400 ml sterile Butterfield Phosphate Buffer solution. The rinsate was collected in a sterile bottle. Ten milliliters of the rinsate was then added to 90 ml of each test solution and to 90 ml of the DI water control. After 5 minutes, 1 ml of each test solution and the DI water control was added in duplicate to APC Petrifilm plates. The inoculated APC Petrifilm plates were incubated at 35.about.37 degrees C. and read after 48 hours. The APC (aerobic plate count) of each inoculated plate is presented below in Table I.

TABLE I

Aerobic Plate Count

| Test Solution | pH | Plate 1 | Plate 2 | Average | Log | Reduction |
|---|---|---|---|---|---|---|
| DI Water | 5 | 360 | 400 | 380 | 2.58 | 0.00 |
| Test solution 1 | 4 | 440 | 360 | 400 | 2.60 | 0.00 |
| Test solution 2 | 3 | 350 | 330 | 340 | 2.53 | 0.05 |
| Test solution 3 | 2 | 15 | 11 | 13 | 1.11 | 1.47 |
| Test solution 4 | 1 | 0 | 0 | 0 | 0.00 | 2.58 |

Figure 6:
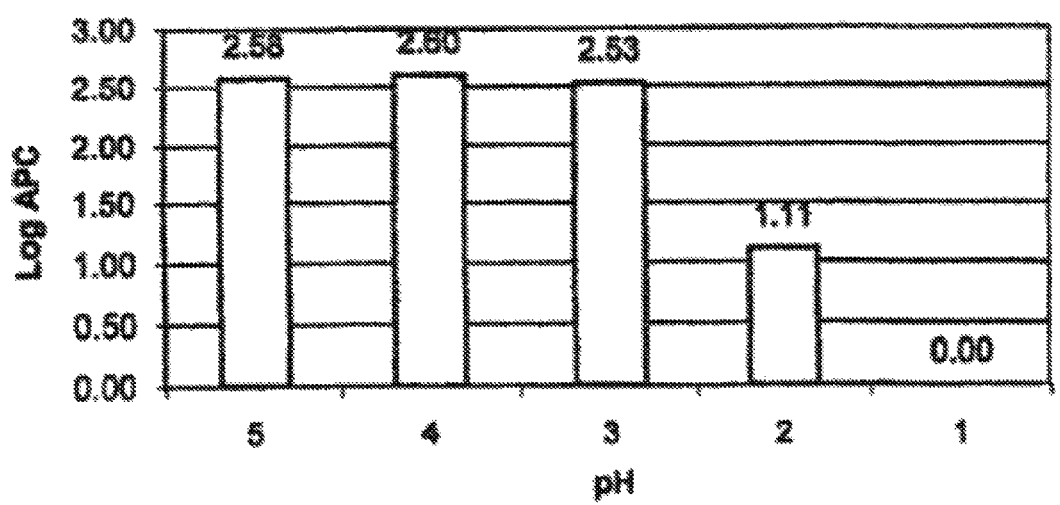
FIG. 6 is a bar graph which illustrates reduction in microbial contamination of culture plates inoculated with the test solutions relative to microbial contamination of culture plates inoculated with the DI water control in implementation of a surface sanitation formulation embodiment of the animal lesion treatment and prevention formulation.

The reduction in microbial contamination of the plates inoculated with the test solutions relative to microbial contamination of plates inoculated with the DI water control is presented in graphical form in FIG. 6. Accordingly, it will be appreciated by those skilled in the art that the surface sanitation formulation without the antimicrobial metal is capable of reducing microbial contamination of a surface to which the formulation is applied.

It will be appreciated by those skilled in the art that the magnesium sulfate in the animal lesion treatment and prevention formulations acts as an effective acid/base buffer to maintain the pH of the formulation solution within an acidic range (typically about 1~4) and facilitate and maintain complete or almost complete dissolution of the antimicrobial metal salt ions in the formulation solution in spite of the addition of large organic loads and other basic materials into the solution. It has been found, for example, that magnesium sulfate as acid/base buffer in the formulation, when combined with heavy metal salt(s) in a range of from about 5 to about 30 lbs. per 50 gallons of water, maintains low pH and keeps heavy antibacterial metals in solution despite the addition of heavy organic loads after the passage of 500 or more cattle through a 50-gallon volume of the footbath solution. Consequently, the antimicrobial properties of the antimicrobial metal salt in the formulation are sustained and precipitation of the antimicrobial metal salt out of solution is prevented or minimized. Furthermore, because the antimicrobial metal salt remains in solution, animal-raising facilities can use less heavy metal salt that would otherwise be required. Consequently, precipitation of the metal or metals in lagoons and soil and runoff of the metal or metals into lakes, rivers, streams and other waterways is minimized.

When the formulation is applied to soft tissue foot lesions of bovines throughout a treatment regimen, the formulation does not tend to irritate the lesions (even at pH of less than 1.0) and may promote soothing and healing of the lesions by rapid drying. This results in rapid reduction in pain scores, resulting in improved animal mobility and an increase in feed/water intake and milk production. In animals with healthy hooves, the formulation may help prevent digital dermatitis and interdigital phlegmon (foot rot) by maintaining healthy hoof conditions. The drying properties of the formulation may enhance hoof hardness and render soft tissue of hooves invulnerable to bacterial infection.

The present disclosure is further directed to a dry formulation mix which may be added to an acid/base buffer and water to form a formulation solution. In some applications, the formulation solution may be used as a footbath solution which is placed in a footbath container. One or more lesion-affected areas on an animal may be immersed in the formulation solution such as by walking the animal through the formulation solution, for example and without limitation, to treat and/or prevent bacterial infections. The formulation solution may be amenable to a variety of other applications such as topical treatment of lesions or other affected areas, as was heretofore described with respect to the flow diagram 200 in FIG. 2 or surface sanitation treatment as was heretofore described with respect to the flow diagram 300 in FIG. 3, for example and without limitation. In some embodiments, the acid/base buffer with which the dry formulation mix is added to the water in preparation of the formulation solution may be a concentrated formulation concentrate which is prepared according to block 102 in FIG. 1, as was described herein above. In other embodiments, the acid/base buffer may be any other suitable type of acid/base buffer.

The dry formulation mix may be used as a replacement for stand-alone use of copper sulfate and zinc sulfate as the antimicrobial metal salt in a footbath solution. Use of the dry formulation mix may reduce the quantity of the heavy metals copper and/or zinc in lagoons and soils. The dry formulation mix may exhibit enhanced dissolving properties over that which is attained using stand-alone copper sulfate and/or zinc sulfate as the antimicrobial metal salt as well as improved buffering capability, enhanced footbath life and improved hoof drying and hardening properties.

The dry formulation mix may include a mixture of copper sulfate pentahydrate, zinc sulfate monohydrate and magnesium sulfate heptahydrate. In some embodiments, the dry formulation mix may include sodium bisulfate, sulfamic acid and/or other acid in a dry or solid acid form. In some embodiments, the dry formulation mix may include a flow aid such as zeolite, for example and without limitation, to enhance the flow characteristics of the mix.

In some embodiments, the copper sulfate pentahydrate may be provided in the dry formulation mix in a quantity of from about 20% to about 70% and preferably, about 40% by weight. The zinc sulfate monohydrate may be present in the dry formulation mix in a quantity of from about 10% to about 50% and preferably, about 30% by weight. The magnesium sulfate heptahydrate may be present in the dry formulation mix in a quantity of from about 5% to about 40% and preferably, about 27% by weight. The sodium bisulfate may be present in the mix in a quantity of from about 1% to about 5% and preferably, about 2% by weight. The flow aid may be present in the mix in a quantity of from about 0.5% to about 2% and preferably, about 1% by weight. The quantities and weight percentages of the components in the dry formulation mix are presented in tabular form in Table II below.

TABLE II

| Dry Formulation Mix Component | Preferred Wt. % | Wt. % Range |
|---|---|---|
| Copper Sulfate Pentahydrate | 40% | 20-70% |
| Zinc Sulfate Monohydrate | 30% | 10-50% |
| Magnesium Sulfate Heptahydrate | 27% | 5-40% |
| Sodium Bisulfate | 2% | 1-5% |
| Flow Aid | 1% | 0.5-2% |

The present disclosure is further directed to an animal lesion treatment and prevention formulation which is prepared using a dry formulation mix. An illustrative embodiment of the animal lesion treatment and prevention formulation may include a footbath solution having a supply of footbath water and a dry formulation mix and an acid/base buffer provided in the footbath water. In some embodiments, the acid/base buffer may include a formulation concentrate having at least one acid which may include at least one of sulfuric acid, a sulfuric acid derivative and sodium bisulfate, for example and without limitation; magnesium sulfate as acid/base buffer; and a quantity of water. The dry formulation mix may include copper sulfate pentahydrate, zinc sulfate monohydrate and magnesium sulfate heptahydrate. In some embodiments, an acid such as sodium bisulfate, sulfamic acid and/or other dry or solid acid form, for example and without limitation, and/or a flow aid such as zeolite, for example and without limitation, may be included in the dry formulation mix. The copper sulfate pentahydrate, the zinc sulfate monohydrate, the magnesium sulfate heptahydrate, the sodium bisulfate and the zeolite may be present in the dry formulation mix in the proportions presented in Table II (above).

The dry formulation mix and the acid/base buffer may be placed in the footbath water in any quantity which is suitable to impart antimicrobial properties to the resulting footbath solution. In some embodiments, the dry formulation mix may be added to the footbath water in a quantity of from about 0.1 lbs. to about 0.6 lbs., and preferably about 0.3 lbs. per gallon of footbath water. In some embodiments, the formulation concentrate or other acid/base buffer may be added to the footbath water in a quantity of from about 0.25 oz to about 0.75 oz, and preferably about 0.50 oz. formulation concentrate or acid/base buffer per gallon of footbath water. For a 50-gallon footbath, a minimum of about 15 lbs. of the dry formulation mix may be present in 50 gallons of footbath water.

Referring next to FIG. 7 of the drawings, flow diagram 700 which illustrates preparation of an illustrative embodiment of a dry formulation mix is illustrated. In block 702, copper sulfate pentahydrate is provided. In block 704, zinc sulfate monohydrate is provided. In block 706, magnesium sulfate heptahydrate is provided. In block 708, in some embodiments an acid in dry or solid form, such as sodium bisulfate and/or sulfamic acid, for example and without limitation, may be provided. In block 710, in some embodiments a flow aid such as zeolite, for example and without limitation, may be provided. In block 712, a dry formulation mix is prepared by thoroughly mixing the copper sulfate pentahydrate, the zinc sulfate monohydrate, the magnesium sulfate heptahydrate, the sodium bisulfate and the flow aid.

Referring next to FIG. 8 of the drawings, a flow diagram 800 of an illustrative embodiment of an animal lesion treatment and prevention method in which the animal lesion treatment and prevention formulation is prepared using a dry formulation mix is illustrated. In block 802, an acid/base buffer is provided. In some embodiments, the acid/base buffer may be a formulation concentrate which is prepared according to block 102 in the flow diagram 100 of FIG. 1. In other embodiments, the acid/base buffer may be any alternative type of acid/base buffer which is suitable for the purpose. In block 804, a dry formulation mix is provided. The dry formulation mix may be prepared according to the flow diagram 700 in FIG. 7. In block 806, footbath water is provided. In block 808, the acid/base buffer which was provided in block 802 is placed with the dry formulation mix which was provided in block 804 in the footbath water. In block 810, a footbath solution is prepared by mixing the acid/base buffer and the dry formulation mix in the footbath water. In block 812, a footbath container is provided. In block 814, the footbath solution which was prepared in block 810 is placed in the footbath container. In block 816, one or more lesion-affected areas on an animal is/are immersed in the footbath solution.

The present disclosure is further directed to a copper-free formulation mix which may be added to an acid/base buffer and water to form a formulation solution. In some applications, the formulation solution may be used as a footbath solution which is placed in a footbath container. One or more lesion-affected areas on an animal may be immersed in the formulation solution such as by walking the animal through the formulation solution, for example and without limitation, to treat and/or prevent bacterial infections. The formulation solution may be amenable to a variety of other applications such as topical treatment of lesions or other affected areas, as was heretofore described with respect to the flow diagram 200 in FIG. 2 or surface sanitation treatment as was heretofore described with respect to the flow diagram 300 in FIG. 3, for example and without limitation. In some embodiments, the acid/base buffer with which the copper-free formulation mix is added to the water in preparation of the formulation solution may be a concentrated formulation concentrate which is prepared according to block 102 in FIG. 1, as was described herein above. In other embodiments, the acid/base buffer may be any other suitable type of acid/base buffer.

The copper-free formulation mix may include a mixture of zinc sulfate monohydrate and magnesium sulfate heptahydrate. In some embodiments, the copper-free formulation mix may include sodium bisulfate, sulfamic acid and/or other acid in a dry or solid acid form. In some embodiments, the copper-free formulation mix may include a flow aid such as zeolite, for example and without limitation, to enhance the flow characteristics of the mix.

In some embodiments, the zinc sulfate monohydrate may be present in the copper-free formulation mix in a quantity of from about 50% to about 90% and preferably, about 70%. The magnesium sulfate heptahydrate may be present in the copper-free formulation mix in a quantity of from about 5% to about 40% and preferably, about 27%. The sodium bisulfate may be present in the mix in a quantity of from about 1% to about 5% and preferably, about 2%. The flow aid may be present in the mix in a quantity of from about 0.5% to about 2% and preferably, about 1%. The quantities and weight percentages of the components in the copper-free formulation mix are presented in tabular form in Table III below.

TABLE III

| Copper-Free Formulation Mix Component | Wt. % | Wt. % Range |
|---|---|---|
| Zinc Sulfate Monohydrate | 70% | 50-90% |
| Magnesium Sulfate Heptahydrate | 27% | 5-40% |

TABLE III-continued

| Copper-Free Formulation Mix Component | Wt. % | Wt. % Range |
|---|---|---|
| Sodium Bisulfate | 2% | 1-5% |
| Flow Aid | 1% | 0.5-2% |

The present disclosure is further directed to an animal lesion treatment and prevention formulation which is prepared using a copper-free formulation mix. An illustrative embodiment of the animal lesion treatment and prevention formulation may include a footbath solution having a supply of footbath water and a copper-free formulation mix and an acid/base buffer provided in the footbath water. In some embodiments, the acid/base buffer may include a formulation concentrate having at least one acid which may include at least one of sulfuric acid, a sulfuric acid derivative and sodium bisulfate, for example and without limitation; magnesium sulfate as acid/base buffer; and a quantity of water. The copper-free formulation mix may include zinc sulfate monohydrate and magnesium sulfate heptahydrate. In some embodiments, an acid in a dry or solid acid form, such as sodium bisulfate and/or sulfamic acid, for example and without limitation, and/or a flow aid such as zeolite, for example and without limitation, may be included in the copper-free formulation mix. The zinc sulfate monohydrate, the magnesium sulfate heptahydrate, the sodium bisulfate and the zeolite may be present in the copper-free formulation mix in the proportions presented in Table I (above).

The copper-free formulation mix may be placed in the footbath water in any quantity which is suitable to impart antimicrobial properties to the resulting footbath solution. In some embodiments, the copper-free formulation mix may be added to the footbath water in a quantity of from about 0.1 lbs. to about 0.6 lbs., and preferably about 0.3 lbs. per gallon of footbath water. In some embodiments, the formulation concentrate or other acid/base buffer may be added to the footbath water in a quantity of from about 0.25 oz to about 0.75 oz formulation concentrate or acid/base buffer per gallon of footbath water to prevent and/or treat infectious bacterial conditions. For a 50-gallon footbath, a minimum of about 15 lbs. of the copper-free formulation mix may be present in 50 gallons of footbath water.

Referring next to FIG. 9 of the drawings, flow diagram 900 which illustrates preparation of an illustrative embodiment of a copper-free formulation mix is illustrated. In block 902, zinc sulfate monohydrate is provided. In block 904, magnesium sulfate heptahydrate is provided. In block 906, in some embodiments an acid in a dry or solid acid form, such as sodium bisulfate and/or sulfamic acid, for example and without limitation, may be provided. In block 908, in some embodiments a flow aid such as zeolite, for example and without limitation, may be provided. In block 910, a copper-free formulation mix is prepared by thoroughly mixing the zinc sulfate monohydrate, the magnesium sulfate heptahydrate, the sodium bisulfate and the flow aid.

Referring next to FIG. 10 of the drawings, a flow diagram 1000 of an illustrative embodiment of an animal lesion treatment and prevention method in which the animal lesion treatment and prevention formulation is prepared using a copper-free formulation mix is illustrated. In block 1002, an acid/base buffer is provided. In some embodiments, the acid/base buffer may be a formulation concentrate which is prepared according to block 102 in the flow diagram 100 of FIG. 1. In other embodiments, the acid/base buffer may be any other type of acid/base buffer which is suitable for the purpose. In block 1004, a copper-free formulation mix is provided. The copper-free formulation mix may be prepared according to the flow diagram 900 in FIG. 9. In block 1006, footbath water is provided. In block 1008, the acid/base buffer which was provided in block 1002 is placed in the footbath water with the copper-free formulation mix which was provided in block 1004. In block 1010, a footbath solution is prepared by mixing the acid/base buffer and the copper-free formulation mix in the footbath water. In block 1012, a footbath container is provided. In block 1014, the footbath solution which was prepared in block 1010 is placed in the footbath container. In block 1016, one or more lesion-affected areas on an animal is/are immersed in the footbath solution to prevent and/or treat infectious bacterial conditions.

While illustrative embodiments of the disclosure have been described above, it will be recognized and understood that various modifications can be made and the appended claims are intended to cover all such modifications which may fall within the spirit and scope of the disclosure.

The invention claimed is:

1. An aqueous formulation for treating or preventing an animal lesion, comprising:
   a first quantity of water;
   sulfuric acid or a sulfuric acid derivative; and
   a solute component comprising zinc sulfate monohydrate, magnesium sulfate heptahydrate, and sodium bisulfate, and optionally a flow aid; wherein,
   the formulation has a pH less than 1.0;
   the formulation does not substantially irritate an animal lesion when applied thereto; and
   zinc sulfate monohydrate is present in a quantity of from about 50% to about 90% by weight of the weight of the solute component; magnesium sulfate heptahydrate is present in a quantity of from about 5% to about 40% by weight of the weight of the solute component; sodium bisulfate in a quantity of from about 1% to about 5% by of the weight of the solute component; and optionally, a flow aid comprising zeolite in a quantity of from about 0.5% to about 2% by weight of the weight of the solute component.

2. An aqueous formulation for treating or preventing an animal lesion, comprising:
   a first quantity of water;
   sulfuric acid or a sulfuric acid derivative; and
   a solute component comprising copper sulfate pentahydrate, zinc sulfate monohydrate, magnesium sulfate heptahydrate, and sodium bisulfate, and optionally a flow aid; wherein,
   the formulation has a pH less than 1.0;
   the formulation does not substantially irritate an animal lesion when applied thereto; and
   copper sulfate pentahydrate is present in a quantity of from about 20% to about 70% by weight of the weight of the solute component; zinc sulfate monohydrate is present in a quantity of from about 10% to about 50% by weight of the weight of the solute component; magnesium sulfate heptahydrate is present in a quantity of from about 5% to about 40% by weight of the weight of the solute component; sodium bisulfate in a quantity of from about 1% to about 5% by weight of the weight of the solute component; and optionally, zeolite in a quantity of from about 0.5% to about 2% by weight of the weight of the solute component.

3. The aqueous formulation of claim 1, wherein magnesium sulfate heptahydrate is present in a quantity of about 27% by weight of the solute component.

4. The aqueous formulation of claim 1, wherein zinc sulfate monohydrate is present in a quantity of about 70% by weight of the solute component.

5. The aqueous formulation of claim 1, wherein sodium bisulfate is present in a quantity of about 2% by weight of the solute component.

6. The aqueous formulation of claim 3, wherein
zinc sulfate monohydrate is present in a quantity of about 70% by weight of the solute component;
sodium bisulfate is present in a quantity of about 2% by weight of the solute component; and
the flow aid is present in a quantity of about 1% by weight of the solute component.

7. The aqueous formulation of claim 2, wherein magnesium sulfate heptahydrate is present in a quantity of about 27% by weight of the solute component.

8. The aqueous formulation of claim 2, wherein copper sulfate pentahydrate is present in a quantity of about 40% by weight of the solute component.

9. The aqueous formulation of claim 2, wherein zinc sulfate monohydrate is present in a quantity of about 30% by weight of the solute component.

10. The aqueous formulation of claim 8, wherein
magnesium sulfate heptahydrate is present in a quantity of about 27% by weight of the solute component;
zinc sulfate monohydrate is present in a quantity of about 30% by weight of the solute component;
sodium bisulfate is present in a quantity of about 2% by weight of the solute component; and
the flow aid is present in a quantity of about 1% by weight of the solute component.

* * * * *